United States Patent [19]

Kane et al.

[11] Patent Number: 4,966,909

[45] Date of Patent: Oct. 30, 1990

[54] 4-BENZYL-5-PHENYL-2,4-DIHYDRO-3H-1,2,4-TRIAZOL-3-ONES AND THEIR USE AS ANTICONVULSANTS

[75] Inventors: John M. Kane, Cincinnati; Francis P. Miller, Loveland, both of Ohio

[73] Assignee: Merrell Dow Pharmaceuticals, Cincinnati, Ohio

[21] Appl. No.: 453,440

[22] Filed: Dec. 20, 1989

[51] Int. Cl.$^5$ ............................................. A61K 31/41
[52] U.S. Cl. ..................................................... 514/359
[58] Field of Search ......................................... 514/359

[56] References Cited

U.S. PATENT DOCUMENTS 4,414,221 11/1983 Parsons et al. ..................... 514/384

FOREIGN PATENT DOCUMENTS

| | | |
|---|---|---|
| 621842 | 2/1963 | Belgium . |
| 894856 | 2/1983 | Belgium . |
| 273309 | 6/1988 | European Pat. Off. . |
| 273310 | 6/1988 | European Pat. Off. . |
| 1126882 | 3/1960 | Fed. Rep. of Germany . |
| 153953 | 2/1982 | German Democratic Rep. . |
| 160447 | 3/1983 | German Democratic Rep. . |
| 6504121 | of 1965 | Netherlands . |
| 651537 | 3/1965 | South Africa . |

OTHER PUBLICATIONS

M. M. Shemyakin, et al., *Tetrahedron* 27 2811–2820 (1971).
Chemical Abstracts 75:88541j. (Syeda Husain, et al., *Indian J. Chem.*, 9(7) 642–6 (1971).
F. P. Miller, et al., FASEB J. 2, A1070, Abstract 4501 (1988).
G. Maffii, et al., Studio Farmacologico Di Alcuni Ossadiazoli E Triazoli, *Farmaco* 13, 629–38 (1958).

*Primary Examiner*—Stanley J. Friedman
*Attorney, Agent, or Firm*—Edlyn S. Simmons

[57] ABSTRACT

The invention relates to 4-benzyl-5-phenyl-1,2,4-dihydro-3H-1,2,4-triazol-3-ones and to their use as anticonvulsants for treatment of seizure disorders.

7 Claims, No Drawings

4-BENZYL-5-PHENYL-2,4-DIHYDRO-3H-1,2,4-TRIAZOL-3-ONES AND THEIR USE AS ANTICONVULSANTS

This invention relates to the use as anticonvulsant agents for the treatment of seizure disorders of 4-benzyl-5-phenyl-2,4-dihydro-3H-1,2,4-triazol-3-ones.

More specifically this invention relates to compounds of the formula

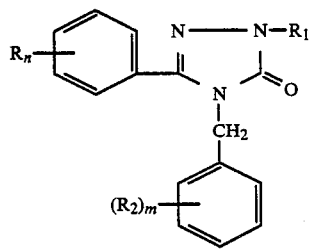

I and the tautomers thereof, wherein
$R_1$ is hydrogen or $C_{1-4}$ lower alkyl;
R and $R_2$ are independently $C_{1-4}$ lower alkyl, $C_{1-4}$ lower alkoxy, halogeno or trifluoromethyl, and m and n are independently zero, 1 or 2;
or $(R_2)_m$ is methylenedioxy.

R and $R_2$ preferably represent halogeno, especially chloro or fluoro, with chloro being more preferred. Compounds wherein R is trifluoromethyl also are preferred. $R_1$ is preferably methyl, although any straight or branched $C_{1-4}$ lower alkyl group may be used. Compounds wherein $R_1$ is hydrogen are also preferred. The tautomeric forms are included for each of the compounds embraced within formula I wherein $R_1$ is H.

Preferably n is one, representing a mono-substituted phenyl moiety with the R-substitutent being located at the ortho, meta or para position, although the ortho- and para-substituted compounds are preferred. When the phenyl moieties are disubstituted (i.e., m or n is 2), substitution may be at the 2,3-; 2,4-; 2,5-; 2,6-; 3,4-; and 3,5-positions. When $(R_2)_m$ is methylenedioxy, substitution may be in either the 2,3- or 3,4-positions of the benzyl group.

The pharmacological profile of these compounds and their relative potencies may readily be demonstrated through standard laboratory tests indicative of compounds known to be useful as anticonvulsants suitable for use in the treatment of seizure disorders. Compounds of formula I are particularly useful for treatment of epilepsy, but their activity in a broad spectrum of laboratory tests is indicative of activity against most types of seizure disorders.

For example, to evaluate and characterize the anticonvulsant and GABAergic activity and to observe the pharmacological profile of the compounds of this invention, it is convenient to employ such tests as the antagonism of 3-mercaptopropionic acid-induced convulsions, an assay performed on mice wherein wild running fits or generalized seizures are induced by 3-mercaptopropionic acid; the antagonism of strychnine-induced seizures in mice, an assay performed in mice wherein seizures are induced by strychnine; the antagonism to maximal electroshock, an assay performed in mice wherein seizures are caused by the administration of electroshock; and the antagonism to pentylenetetrazol, an assay to measure the prevention of seizures caused by administration of pentylenetetrazol.

Compounds that inhibit pentylenetetrazol-induced seizures in mice are known to possess anticonvulsant and antianxiety effects. An appropriate dose of test compound is administered to groups of mice and, at a selected time thereafter, pentylenetetrazol, prepared as a solution in distilled water such that 10 ml/kg delivers a dose of 60 mg/kg, is administered by rapid intravenous injection. Absence of clonic convulsions for 2 minutes after pentylenetetrazol is considered significant protection. Prevention of tonic extensor convulsions is also reported and usually occurs at a dose lower than that required to block clonic convulsions. Inhibition of clonic seizures induced by this dose of pentylenetetrazol is evidence of potential anticonvulsant/antianxiety activity. Against seizures caused by pentylenetetrazol, 5-(4-chlorophenyl)-2,4-dihydro-4-benzyl-2-methyl-3H-1,2,4-triazol-3-one has an $ED_{50}$ of 22.6 mg/kg.

In the test for antagonism to maximal electroshock, small groups of mice are administered one or more doses of test compound. At a selected time thereafter, an electroshock sufficient to cause tonic extension in 100% of control mice is administered by means of corneal electrodes. The shock parameters are 50 mA, 120 V, 0.2 seconds. Inhibition of the tonic extensor component of the electroshock convulsion is indicative of anticonvulsant activity of the test material. Phenobarbital blocks in the dose range of 15–30 mg/kg, diphenylhydantoin in the range of 7.5–15 mg/kg. Both of these compounds are effective versus grand mal epilepsy. In this assay, 5-(4-chlorophenyl)-2,4-dihydro-4-benzyl-2-methyl-3H-1,2,4-triazol-3-one has an $ED_{50}$ between 50 and 100 mg/kg.

Patients suitable for treatment with anticonvulsant compositions containing compounds of formula I include warmblooded animals suffering from seizure disorders, for example, mammals such as humans, dogs, cats, horses, pigs, cattle, sheep, rats and mice. The compounds of this invention will exert anticonvulsant activity useful in the treatment of epilepsy and of other seizure disorders at oral dosage levels of about 0.25 to 25 mg/kg of body weight per day. Such doses are much lower than the doses at which these compounds exhibit sedative action and are well below toxic doses of the compounds. Of course the degree of severity of the disease, the age of the patient and other factors normally considered by the attending diagnostician will influence the individual regimen for each patient. In general, the parenterally administered doses are about ¼ to ½ those of orally administered doses.

For oral administration the compounds can be formulated into solid or liquid preparations such as capsules, pills, tablets, troches, powders, solutions, suspensions or emulsions. Solid unit dosage forms can be in the form of a capsule which can be of the ordinary gelatin type containing, for example, lubricants and inert fillers such as lactose, sucrose or cornstarch. In another embodiment the compounds of general formula I can be tableted with conventional tablet bases such as lactose, sucrose and cornstarch, in combination with binders such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohol, oils and other acceptable organic solvents, with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol, glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic ®, a silicone rubber manufactured by the Dow-Corning Corporation.

As is true for most classes of compounds generally suitable as therapeutic agents, certain subgeneric groups and specific members of that class, in the light of their overall biological profile, are preferred. In this instance the preferred R substituent is chloro, with chloro at the 2- or 4-positions of the aromatic ring being preferred. It is preferred that the $R_2$ substituent be chloro, fluoro or trifluoromethyl when m is one or two, with hydrogen and methyl being the preferred groups for $R_1$. A particularly preferred compound is 5-(4-chlorophenyl)-2,4-dihydro-4-benzyl-2-methyl-3H-1,2,4-triazol-3-one.

The compounds of Formula I may readily be prepared using processes and techniques analogously known in the art, for example in the method of S. Kuboda and M. Uda, *Chem. Pharm. Bull.* 21, 1342 (1979), as seen by the following reaction scheme:

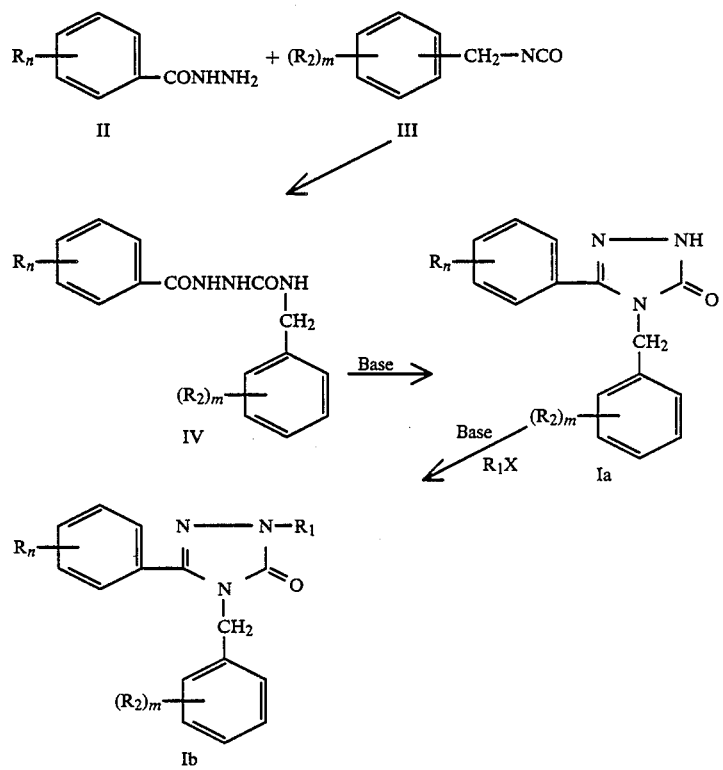

wherein R, n, m, $R_1$ and $R_2$ are as defined in formula I, and X is a suitable leaving group.

The preparation of the 1-benzoyl-4-benzyl-semicarbazides (IV) is readily effected by reacting a hydrazide (II) with a benzylisocyanate (III) by contacting the reactants together in a suitable aprotic solvent, preferably one in which the hydrazide reactant is soluble, e.g., tetrahydrofuran (THF), $CHCl_3$, $CH_2Cl_2$, benzene, toluene, $Et_2O$ and the like. The reaction is quite rapid and may be carried out at from 0° C. to about room temperature and, although the reaction proceeds rapidly, the mixture may be left for 24 hours without any significant decrease in yield. The required hydrazides and isocyanates are readily available, but may be prepared by known techniques quite obvious to one of ordinary skill in the art.

The desired 4-benzyl-5-phenyl-2,4-dihydro-3H-1,2,4-triazol-3-ones (Ia) may be prepared by reacting the semicarbazides (IV) with a base, preferably an aqueous alkali metal hydroxide (e.g., NaOH, KOH) at about 50°-120° C., although reflux temperatures are preferred. Normal reaction time is about 7 hours, although 4-24 hours may be needed depending on the temperature of the mixture and the structure of the reactant.

The desired 2,4-disubstituted-2,4-dihydro-3H-1,2,4-triazol-3-ones (Ib) may be prepared by reacting the 4-benzyl-5-phenyl-2,4-dihydro-3H-1,2,4-triazol-3-ones (Ia) with an appropriate $R_1X$ reactant wherein X is a suitable leaving group, e.g., Cl, Br, $OSO_2CF_3$ and the like. Preferably the reaction takes place in a solution of an aqueous alkali metal hydroxide, (e.g., KOH, NaOH) although more reactive bases (e.g., NaH, KH, LDA) may be used if the reaction is affected under aprotic dry conditions. The reaction preferably takes place at room temperatures over periods of about 18 hours to two weeks.

The following specific examples are given to illustrate the preparation of the compounds of this invention.

Preparation of Intermediate
1-Benzoyl-4-benzylsemicarbazides

EXAMPLE 1

1-(4-Chlorobenzoyl)-4-benzylsemicarbazide

A stirred suspension of 4-chlorobenzoic acid, hydrazide (10.4932 g, $6.1508 \times 10^{-2}$ mole) and dry THF (240 mL) was warmed with a heat gun until it was homogenous. To this stirred solution was added benzyl isocyanate (7.8 ml, $6.3 \times 10^{-2}$ mole). After stirring overnight at room temperature, the reaction was diluted with ether. The precipitate was collected by filtration, washed with a little ether, and dried by suction Crystallization from ethanol afforded small colorless needles 15.69 g (84%), mp 244°–246° C.

Preparation of
5-Phenyl-4-benzyl-2,4-dihydro-3H-1,2,4-triazol-3-ones

EXAMPLE 2

4-Benzyl-5-(4-chlorophenyl)2,4-dihydro-3H-1,2,4-triazol-3-one

A stirred mixture of 1-(4-chlorobenzoyl)-4-benzylsemicarbazide (16.15 g, $5.317 \times 10^{-2}$ mole) and 1 molar aqueous NaOH (64 ml, $6.4 \times 10^{-2}$ mole) was heated to reflux. After refluxing ca. 22 hrs., the reaction was allowed to cool slightly before being neutralized by the addition of concentrated aqueous HCl (5.5 ml, $6.6 \times 10^{-2}$ mole). A colorless solid formed and after the mixture had cooled to room temperature this was collected by filtration. Crystallization from isopropanol afforded colorless needles: 12.76 g (84%), mp. 208°–210° C.

Preparation of
5-Phenyl-2-substituted-4-benzyl-2,4-dihydro-3H-1,2,4-triazol-3-ones

EXAMPLE 3

5-(4-Chlorophenyl)-2-methyl-4-benzyl-2,4-dihydro-3H-1,2,4-triazol-3-one

To a stirred, room temperature, suspension of 4-benzyl-5-(4-chlorophenyl)-3H-1,2,4-triazol-3-one (10.85 g, $3.797 \times 10^{-2}$ mole), 1 molar aqueous NaOH (42 ml, $4.2 \times 10^{-2}$ mole), and ethanol (15 ml) was added methyl iodide (3.6 ml, $5.8 \times 10^{-2}$ mole). After stirring overnight, the reaction was transferred to a separatory funnel where it was extracted with EtOAc (3x). The EtOAc extracts were combined, washed with saturated aqueous NaCl, and dried over anhydrous $Na_2SO_4$. The drying agent was removed by filtration and the filtrate was evaporated at reduced pressure leaving a yellowish foam. Purification of this foam by a combination of flash chromatography (20% $EtOAc/CH_2Cl_2$) and crystallization from cyclohexane afforded colorless crystals 5.92 g (52%), mp 90°–91° C.

In a similar manner the following compounds also may be prepared.

| $R_n$—Ar | $R_1$ | $(R_2)_m$ | mp (°C.) |
|---|---|---|---|
| Phenyl | H | 2,4-$Cl_2$ | 145–146 |
| Phenyl | $CH_3$ | 2,4-$Cl_2$ | 112–114 |
| 4-Chlorophenyl | H | 2,4-$Cl_2$ | 189–191 |
| 4-Chlorophenyl | $CH_3$ | 2,4-$Cl_2$ | 104–106 |

What is claimed is:

1. A method for the treatment of seizure disorders which comprises administering to a patient in need thereof an anticonvulsant amount of a compound of the formula wherein
$R_1$ is hydrogen or $C_{1-4}$ lower alkyl;
R and $R_2$ are independently $C_{1-4}$ lower alkyl, $C_{1-4}$ lower alkoxy, halogeno or trifluoromethyl; and
m and n are independently zero, 1 or 2;
or $(R_2)_m$ is methylenedioxy.

2. A method of claim 1 wherein $R_1$ is hydrogen or methyl.
3. A method of claim 1 wherein m is 1 or 2 and $R_2$ is halogen.
4. A method of claim 1 wherein m is 0.
5. A method of claim 1 wherein n is 1 or 2 and R is halogeno.
6. A method of claim 5 wherein R is chloro.
7. A method of claim 6 wherein the compound is 5-(4-chlorophenyl)-2,4-dihydro-4-benzyl-2-methyl-3H-1,2,4-triazol-3-one.

* * * * *